US009067200B2

(12) United States Patent
Nagai et al.

(10) Patent No.: US 9,067,200 B2
(45) Date of Patent: Jun. 30, 2015

(54) METHOD FOR PRODUCING SUBSTITUTED FLUORINE-CONTAINING OLEFIN

(75) Inventors: Takabumi Nagai, Settsu (JP); Takashi Shibanuma, Settsu (JP); Sensuke Ogoshi, Suita (JP); Masato Ohashi, Suita (JP)

(73) Assignees: DAIKIN INDUSTRIES, LTD., Osaka (JP); OSAKA UNIVERSITY, Osaka (JP)

( * ) Notice: Subject to any disclaimer, the term of this patent is extended or adjusted under 35 U.S.C. 154(b) by 0 days.

(21) Appl. No.: 13/581,849

(22) PCT Filed: Mar. 3, 2011

(86) PCT No.: PCT/JP2011/054973
§ 371 (c)(1),
(2), (4) Date: Aug. 30, 2012

(87) PCT Pub. No.: WO2011/108668
PCT Pub. Date: Sep. 9, 2011

(65) Prior Publication Data
US 2012/0330072 A1    Dec. 27, 2012

(30) Foreign Application Priority Data

Mar. 3, 2010  (JP) ................................. 2010-046866
Oct. 13, 2010  (JP) ................................. 2010-230843

(51) Int. Cl.
C07C 17/263    (2006.01)
C07C 17/266    (2006.01)
C07C 22/08     (2006.01)
B01J 23/89     (2006.01)

(52) U.S. Cl.
CPC ........... *B01J 23/892* (2013.01); *C07C 17/2632* (2013.01)

(58) Field of Classification Search
USPC ....................................................... 570/144
See application file for complete search history.

(56) References Cited

U.S. PATENT DOCUMENTS

2002/0062049 A1    5/2002  Wood
2008/0194842 A1*   8/2008  Guiles et al. .................... 549/78

FOREIGN PATENT DOCUMENTS

| CN | 1468206     | 1/2004  |
|----|-------------|---------|
| JP | 60-72833    | 4/1985  |
| JP | 2003-146927 | 5/2003  |
| JP | 2006-16366  | 1/2006  |
| JP | 2007-045729 | 2/2007  |
| JP | 2009-067726 | 4/2009  |
| JP | 2010-229129 | 10/2010 |

OTHER PUBLICATIONS

Xi-kui, J. et al. Chemistry of trifluorostyrenes and their dimers 2. Synthesis of substituted α,β,β-trifluorostyrenes and α,β,β-trifluoroethenylnaphthalenes. Hammett correlations of their NMR parameters and the concept of "distorted π-electron clouds". Acta Chimica Sinica, 1983, 1, 42-49.*
Ohashi, M. et al. Journal of American Chemical Society, 2011, 133, 3256-3259, Published Feb. 15, 2011; only supporting information pp. S1-S11.*
International Search Report issued Jun. 7, 2011 in International (PCT) Application No. PCT/JP2011/054973, of which the present application is the national stage.
Ohashi et al., "Palladium-Catalyzed Coupling Reactions of Tetrafluoroethylene with Arylzinc Compounds", Journal of the American Chemical Society, vol. 133, Feb. 15, 2011, pp. 3256-3259.
Tamao et al., "Nickel-Phosphine Complex-Catalyzed Grignard Coupling. I. Cross-Coupling of Alkyl, Aryl, and Alkenyl Grignard Reagents with Aryl and Alkenyl Halides: General Scope and Limitations", Bulletin of the Chemical Society of Japan, vol. 49, No. 7, 1976, pp. 1958-1969.
Aoki et al., "Synthesis and polymerization of *p*-pentamethyldisiloxanyl-α,β,β-trifluorostyrene and oxygen permeability of the polymer", Journal of Fluorine Chemistry, vol. 59, 1992, pp. 285-288.
Jiang et al., "Chemistry of Trifluorostyrenes and Their Dimers Part 2., Structure-Property Relation of Fluoroolefms: V. Synthesis of Substituted α,β,β-Trifluorostyrenes and α,β,β-Trifluoroethenyl-naphthalenes-Hammett Correlations of Their $^{19}$FNMR Parameters and the Concept of Distorted π-Electron Clouds", No. 3, 1982, pp. 199-201.
Drakesmith et al., "The Preparation and Reactions of Some Fluorine-Containing Vinyl Organometallic Compounds", The Journal of Organic Chemistry, vol. 33, No. 1, Jan. 1968, pp. 286-291.
Kaesz et al., "Synthesis and Cleavage of Perfluorovinyltin Compounds", Journal of the American Chemical Society, vol. 82, No. 24, 1960, pp. 6232-6235.
Martinet et al., "Préparation et réactivité de Et$_3$SiCF=CFM (M= Li, ZnBr)", Journal of Organometallic Chemistry, vol. 367, 1989, pp. 1-10.
Dixon, "Elimination Reaction of Fluoroölefins with Organolithium Compounds" Journal of Organic Chemistry, vol. 21, No. 4, 1956, pp. 400-403.
Xi-Kui et al., Structure-Property Relationships of Fluoroolefins: Synthesis of Substituted α,β,β-Trifluorostyrenes,α,β,β-Trifluoroethenylnaphthalenes Hammett Correlations of Their $^{19}$FNMR Parameters and the Concept of "Distorted π-Electronclouds", Huaxue Xuebao, vol. 41, No. 7, 1983, pp. 637-647.
Burdon et al., "The reactivity of the hydrofluorocarbon 1,1,1,2-tetrafluoroethane (HFC-134a) and related compounds towards base attack. The generation and stability of the tetrafluoroethyl, trifluorovinyl and related anions", Journal of Fluorine Chemistry, vol. 99, 1999, pp. 127-131.

(Continued)

*Primary Examiner* — Fereydoun G Sajjadi
*Assistant Examiner* — Medhanit Bahta
(74) *Attorney, Agent, or Firm* — Wenderoth, Lind & Ponack, L.L.P.

(57) ABSTRACT

This invention relates to a method of reacting fluoroolefin with an organic magnesium compound in the presence of a catalyst comprising nickel or palladium so as to efficiently produce fluoroolefin, such as TFE, in which a fluorine (F) atom or atoms bonded to the sp$^2$ hybridized carbon atom are substituted with an organic group.

12 Claims, No Drawings

(56) References Cited

OTHER PUBLICATIONS

Lim et al. "Synthesis of Novel d-2'-Deoxy-2'-C-difluoromethylene-4'-thiocytidine as a Potential Antitumor Agent", Organic Letters, vol. 4, No. 4, 2002, pp. 529-531.

Florian F. Kneisel et al., "Nucleophilic Catalysis of the Iodine-Zinc Exchange Reaction: Preparation of Highly Functionalized Diaryl Zinc Compounds", Angew. Chem. Int. Ed., 2004, vol. 43, pp. 1017-1021.

Arkady Krasovskiy et al., "Highly Efficient Reagents for Br/Mg Exchange", Angew. Chem. Int. Ed., 2006, vol. 45, pp. 159-162.

Hongjun Ren et al., Stereoselective Preparation of Functionalized Acyclic Alkenylmagnesium Reagents Using $i$-PrMgC1-LiC1, Organic Letters, 2004, vol. 6, No. 23, pp. 4215-4217.

Patent Office of The People's Republic of China, Notification of Third Office Action mailed Apr. 20, 2015 in corresponding Chinese Application No. 201180012061.4, with partial English translation.

\* cited by examiner

METHOD FOR PRODUCING SUBSTITUTED FLUORINE-CONTAINING OLEFIN

TECHNICAL FIELD

The present invention relates to a method for producing a fluoroolefin substituted with an organic group. More specifically, the present invention relates to a method for producing a fluoroolefin substituted with an organic group by selectively substituting a fluorine (F) atom or atoms bonded to the $sp^2$ hybridized carbon atom of a fluoroolefin atom with an organic group using a transition metal complex such as palladium (Pd), nickel (Ni) or the like, as a catalyst.

BACKGROUND ART

For example, the following methods have been reported as methods for producing substituted fluoroolefins.

Non-Patent Document 1 discloses a method for first converting a carbon-halogen (C—X) bond of $CF_2$=CFX (X: halogen atom other than fluorine atom) into a carbon-lithium (C—Li) bond by butyllithium, and then performing C—C bond forming reaction.

Non-Patent Documents 2 and 3 disclose a method for further converting Li of the carbon-lithium (C—Li) bond formed as above into a metal such as Sn, Si, or the like, and then performing C—C bond forming reaction.

However, these methods are not regarded as practical because $CF_2$=CFX used as a raw material is not easily obtainable and relatively expensive. Further, because the fluorine-containing lithium reagent containing the C—Li bond formed at the first stage is very unstable, it is necessary to conduct the reaction under a low temperature of about −100° C.

Non-Patent Documents 4 to 6 disclose a method of reacting tetrafluoroethylene (TFE) with an organic lithium reagent or an aryl magnesium reagent, thereby selectively substituting a fluorine atom. Ph represents phenyl.

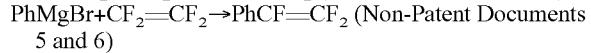

To ensure desired selectivity in obtaining a desired product from TFE, it is necessary to perform the reaction at a low temperature using a large excess of TFE. When the reaction temperature increases, the progress of the reaction becomes out of control, thereby producing a mixture of 1,2-adducts, products with a larger number of substituents, etc. Consequently, the yield of the desired product greatly decreases.

Non-Patent Document 7 discloses a method of reacting HFC134a ($CF_3CFH_2$) with alkyl lithium and generating a fluorine-containing vinyl lithium by elimination reaction. The resulting fluorine-containing vinyl lithium is then subjected to coupling reaction using a vinyl zinc reagent generated by metal replacement using zinc.

However, this method requires an excess amount of expensive alkyl lithium and also suffers from a difficulty in reaction temperature control due to the instability of the fluorine-containing vinyl lithium produced as an intermediate.

In contrast to these known methods, if it is possible to substitute a fluorine atom (F) bonded to the $sp^2$ hybridized carbon atom in the molecule with an organic group using tetrafluoroethylene (TFE), hexafluoropropene (HFP), etc., which are industrially readily obtainable, in the presence of catalyst such as a transition metal substituent, the method is useful for synthesis of substituted fluoroolefins.

Generally, although many methods for introducing a substituent into a nonfluorinated olefin using a transition metal as a catalyst have been reported in the past, only a few methods perform a reaction that activates a C—F bond in a fluoroolefin, and then generate a C—C bond. This is presumably because the binding energy of the C—F bond in the fluoroolefin is much higher than the C—Y (Y represents Cl, Br, I, or the like) bond of other halogen-containing olefins, and also because the fluorine atom, which is small and hard, makes it difficult to cause cleavage of the C—F bond or oxidative addition reaction of metals with respect to the C—F bond. Moreover, there have been no reports of a catalytic reaction to substitute a fluorine atom (F) of a fluoroolefin with an organic group using a transition metal.

A 1-substituted fluoroolefin, such as 1,1,2-trifluorostyrene is useful for, for example, materials of polyelectrolyte. Further, 1,1-disubstituted fluoroolefin, such as 1,1-difluoro-2,2-diphenylethylene, is useful for, for example, medicinal products such as an enzyme inhibitors or ferroelectric materials. However, a method for easily and efficiently producing these compounds has not been established.

For example, Non-Patent Document 8 reports that a 1,1-disubstituted fluoroolefin can be produced by a difluoromethylenation reaction through a Wittig reaction of a carbonyl compound. However, when ketone is used as a carbonyl compound, the yield is low even with an excess amount of Wittig reagent (at least 4 to 5 equivalents). Further, this method also requires a cancer-causing hexamethylphosphorous triamide as a phosphorous compound. As such, the method has several disadvantages.

Therefore, if it is possible to easily produce substituted fluoroolefin (such as, 1-substituted fluoroolefin, 1,1-disubstituted fluoroolefin, or the like) from a readily obtainable fluoroolefin such as TFE, the method can be very useful as a synthetic method.

PRIOR ART

Non-Patent Documents

[Non-Patent Document 1] P. Tarrant et al., J. Org. Chem. 1968, vol. 33, pp. 286

[Non-Patent Document 2] F. G. A. Stone et al., J. Am. Chem. Soc., 1960, vol. 82, pp. 6232

[Non-Patent Document 3] J-F. Normant et al., J. Organomet. Chem. 1989, vol. 367, pp. 1

[Non-Patent Document 4] S. Dixon, J. Org. Chem., 1956, vol. 21, pp. 400

[Non-Patent Document 5] J. Xikui et al., Huaxue Xuebao, 1983, vol. 41, pp. 637

[Non-Patent Document 6] Aoki et al., J. Fluorine Chem., 1992, vol. 59, pp. 285

[Non-Patent Document 7] J. Burdon et al., J. Fluorine Chem., 1999, vol. 99, pp. 127

[Non-Patent Document 8] L. S. Jeong et al., Organic Letters, 2002, vol. 4, pp. 529

SUMMARY OF INVENTION

Technical Problem

An object of the present invention is to provide a method for efficiently substituting a fluorine atom bonded to the $sp^2$ hybridized carbon atom of a fluoroolefin, such as TFE, with an organic group.

Solution to Problem

The inventors of the present invention attempted to react a fluoroolefin such as TFE with an organic magnesium reagent in the presence of transition metal catalyst such as nickel or palladium, and succeeded in producing a fluoroolefin in which a fluorine atom bonded to the sp² hybridized carbon atom is substituted with an organic group of an organic magnesium reagent.

More specifically, the inventors found that by reacting TFE with a phenyl magnesium reagent (7) in the presence of nickel or palladium serving as a catalyst, α,β,β-trifluorostyrene (4), 1,1-difluoro-2,2-diphenylethylene(5), or the like can be obtained. This reaction is considered to advance through the following catalytic cycle.

[Item 6]

The method according to Item 5, wherein:

the zerovalent palladium complex is at least one member selected from the group consisting of $Pd_2(DBA)_3$ (DBA represents dibenzylideneacetone), $Pd(COD)_2$ (COD represents cycloocta-1,5-diene), Pd(DPPE)(DPPE represents 1,2-bis-diphenylphosphinoethane), $Pd(PCy_3)_2$(Cy represents cyclohexyl), $Pd(Pt—Bu_3)_2$ and $Pd(PPh_3)_4$(Ph represents phenyl), and the phosphine is triarylphosphine or trialkylphosphine.

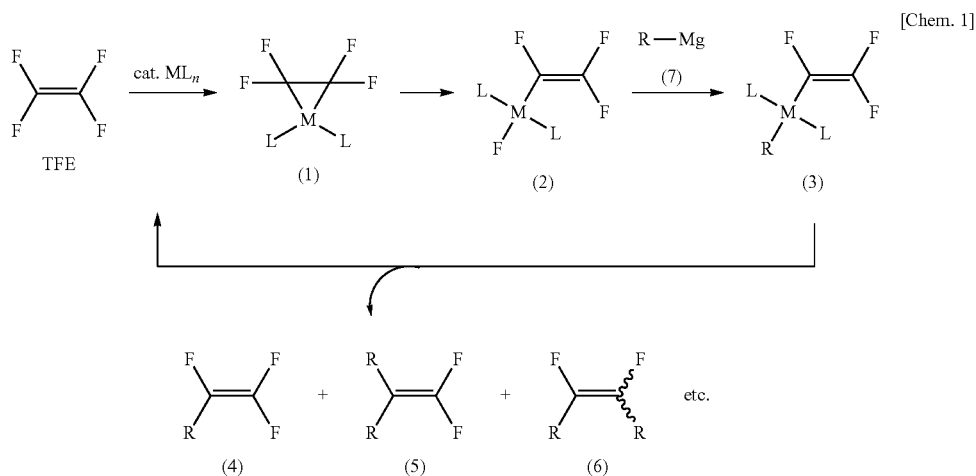

[Chem. 1]

M = Pd or Ni
L = Ligand
R = Ph

By conducting further research based on such a finding, the inventors completed the present invention.

Specifically, the present invention relates to the following methods for producing a substituted fluoroolefin.

[Item 1]

A method for producing fluoroolefin substituted with an organic group, the method comprising reacting fluoroolefin with an organic magnesium compound in the presence of a catalyst comprising nickel or palladium.

[Item 2]

The method according to Item 1, wherein at least one fluorine atom bonded to a sp² hybridized carbon atom of the fluoroolefin is substituted with an organic group derived from the organic magnesium compound.

[Item 3]

The method according to Item 1 or 2, wherein the reaction is performed by further adding a fluorophilic compound and/or by heating.

[Item 4]

The method according to any one of Items 1 to 3, wherein the catalyst comprises palladium.

[Item 5]

The method according to Item 1, wherein the catalyst comprising palladium is a zerovalent palladium complex, a zerovalent palladium complex produced from a divalent palladium complex during the reaction, or a complex obtained by mixing these complexes with at least one compound selected from the group consisting of diketone, phosphine, diamine and bipyridyl.

[Item 7]

The method according to any one of Items 1 to 6, wherein the organic magnesium compound is a compound represented by Formula (7a) and/or Formula (7b):

$$RMgX \quad (7a)$$

$$R_2Mg \quad (7b)$$

wherein R is substituted or unsubstituted aryl or alkyl, X is Cl, Br or I.

[Item 8]

The method according to Item 7, wherein R is alkyl, or mono-, di- or tri-cyclic aryl, the aryl being optionally substituted with at least one member selected from the group consisting of lower alkyl, lower alkenyl, lower alkoxy, and aryl, the alkyl being optionally substituted with at least one member selected from the group consisting of lower alkoxy and aryl.

[Item 9]

The method according to Item 3, wherein when the reaction is performed by adding a fluorophilic compound, the fluorophilic compound is lithium halide, magnesium halide, or zinc halide.

[Item 10]

The method according to Item 1, wherein the method produces a compound represented by Formula (4) and/or Formula (5),

[Chem. 2]

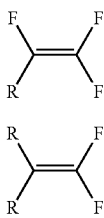

wherein R is substituted or unsubstituted aryl or alkyl,
the method comprising reacting, in the presence of a catalyst comprising nickel or palladium, tetrafluoroethylene with an organic magnesium compound represented by Formula (7a) and/or Formula (7b):

RMgX (7a)

R$_2$Mg (7b)

wherein X is Cl, Br or I, and R is the same as above.
[Item 11]
A method for producing a compound represented by Formula (5′),

[Chem. 3]

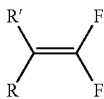 (5′)

wherein, R and R′ are the same or different, and each represents substituted or unsubstituted aryl or alkyl,
the method comprising the steps of:
(i) reacting, in the presence of a catalyst comprising nickel or palladium, tetrafluoroethylene with an organic magnesium compound represented by Formula (7a) and/or Formula (7b):

RMgX (7a)

R$_2$Mg (7b)

wherein X is Cl, Br or I, and R is the same as above, so as to produce a compound represented by Formula (4):

[Chem. 4]

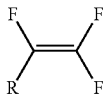 (4)

wherein R is the same as above; and
(ii) reacting, in the presence of a catalyst comprising nickel or palladium, the compound represented by Formula (4) with an organic magnesium compound represented by Formula (7a′) and/or Formula (7b′):

R′MgX′ (7a′)

R′$_2$Mg (7b′)

wherein X is Cl, Br or I, and R′ is the same as above,
so as to produce the compound represented by Formula (5′).

[Item 12]
A method for producing a compound represented by Formula (4a),

[Chem. 5]

 (4a)

wherein R represents substituted or unsubstituted aryl or alkyl,
the method comprising reacting, in the presence of a catalyst comprising nickel or palladium, tetrafluoroethylene with an organic magnesium compound represented by Formula (7a) and/or Formula (7b):

RMgX (7a)

R$_2$Mg (7b)

wherein X is Cl, Br or I, and R is the same as above.

Effects of Invention

The method of the present invention makes it possible to efficiently substitute a fluorine atom bonded to the sp$^2$ hybridized carbon atom of a fluoroolefin with an organic group such as aryl or alkyl. In particular, by using TFE as a raw material, it is possible to efficiently synthesize 1-substituted fluoroolefin and 1,1-disubstituted fluoroolefin.

Further, as disclosed in Non-Patent Documents 4 and 6, the addition elimination reaction of TFE with an alkyl metal reagent only produces 1,2-disubstituted fluoroolefin and cannot produce 1,1-disubstituted fluoroolefin. In the present invention, it appears that the substitution reaction of the C—F bond advances after the formation of a transition metal-fluorine-containing vinyl complex. Thereby, selective production of 1,1-disubstituted fluoroolefin is possible.

DESCRIPTION OF EMBODIMENTS

The method of the present invention reacts a fluoroolefin and an organic magnesium compound in the presence of a catalyst comprising nickel or palladium, thereby efficiently producing a fluoroolefin substituted with an organic group.

Examples of fluoroolefins used in the present invention as a substrate include compounds in which at least one fluorine atom is bonded to the two sp$^2$ hybridized carbon atoms of the olefin. More specifically, the examples include tetrafluoroethylene (TFE), hexafluoropropylene (HFP), trifluoroethylene, 1,1-difluoroethylene (vinylidene fluoride), and 1,2-difluoroethylene. In view of ready availability, versatility in fluorine chemistry, etc., TFE, trifluoroethylene, and the like are preferable.

Examples of catalysts containing nickel or palladium include nickel complexes and palladium complexes. These complexes are used both as reagents to be added and as reaction products (catalytically active species).

Examples of palladium complexes include zerovalent palladium complexes, zerovalent palladium complexes produced from divalent palladium complexes during reaction, and complexes obtained by mixing these complexes with at least one compound (ligand) selected from the group consisting of diketone, phosphine, diamine and bipyridyl.

Zerovalent palladium complexes are not limited, and examples thereof include $Pd_2(DBA)_3$ (DBA represents dibenzylideneacetone), $Pd(COD)_2$ (COD represents cycloocta-1,5-diene), Pd(DPPE)(DPPE represents 1,2-bisdiphenylphosphinoethane), $Pd(PCy_3)_2$(Cy represents cyclohexyl), $Pd(Pt—Bu_3)_2$, and $Pd(PPh_3)_4$(Ph represents phenyl).

Examples of divalent palladium complexes include palladium chloride, palladium bromide, palladium acetate, bis(acetylacetonato)palladium(II), dichloro($\eta^4$-1,5-cyclooctadiene)palladium(II), and complexes in which a phosphine ligand such as triphenylphosphine is coordinated to these palladium complexes. These divalent palladium complexes are reduced, for example, by co-existing reduction species (phosphine, zinc, or organometallic reagent, etc.) during reaction, thereby producing zerovalent palladium complexes.

The aforementioned zerovalent palladium complexes and zerovalent palladium complexes produced from divalent palladium complexes during reaction may be converted into zerovalent palladium complexes that are involved in reaction by acting on the compound (ligand) such as diketone, phosphine, diamine, or bipyridyl that are added during the reaction as necessary. The number of ligands coordinated to a zerovalent palladium complex during reaction is not necessarily known.

Examples of diketones include β-diketones such as acetylacetone, 1-phenyl-1,3-butanedione, or 1,3-diphenylpropanedion.

Preferable examples of phosphines are trialkylphosphine and triarylphosphine. Examples of trialkylphosphine include tri(C3-20 alkyl)phosphine such as tricyclohexylphosphine, triisopropylphosphine, tri-t-butylphosphine, trithexylphosphine, triadamantylphosphine, tricyclopentylphosphine, di-t-butylmethylphosphine, tribicyclo[2,2,2]octylphosphine, and trinorbornylphosphine. Examples of triarylphosphine include tri(monocyclic aryl)phosphine such as triphenylphosphine, trimesitylphosphine, and tri(o-tolyl)phosphine. Among these, triphenylphosphine, tricyclohexylphosphine, and tri-t-butylphosphine are preferable. Additionally, bidentate ligands such as 1,4-bis(diphenylphosphino)butane, 1,3-bis(diphenylphosphino)propane, and 1,1'-bis(diphenylphosphino)ferrocene may also be used.

Examples of diamines include tetramethylethylenediamine, 1,2-diphenylethylenediamine, and the like.

Among these ligands, phosphine, diamine, and bipyridyl are preferable. Triarylphosphine is more preferable. Triphenylphosphine is particularly preferable. Generally, it is possible to more efficiently obtain the target substituted fluoroolefin by using a palladium complex having a bulky ligand, such as phosphine.

Examples of nickel complexes include zerovalent palladium complexes, zerovalent palladium complexes produced from divalent palladium complexes during reaction, and complexes obtained by mixing these complexes with at least one compound (ligand) selected from the group consisting of diketone, phosphine, diamine and bipyridyl.

Zerovalent nickel complexes are not limited, and examples thereof include $Ni(COD)_2$, $Ni(CDD)_2$ (CDD represents cyclodeca-1,5-diene), $Ni(CDT)_2$ (CDT represents cyclodeca-1,5,9-triene), $Ni(VCH)_2$ (VCH represents 4-vinyl cyclohexene), $Ni(CO)_4$, $(PCY_3)_2Ni—N\equiv N—Ni(PCy_3)_2$, and $Ni(PPh_3)_4$.

Examples of divalent nickel complexes include nickel chloride, nickel bromide, nickel acetate, bis(acetylacetonato)nickel(II), and complexes in which a phosphine ligand such as triphenylphosphine is coordinated to these nickel complexes. These divalent nickel complexes are reduced, for example, by co-existing reduction species (phosphine, zinc, or organometallic reagent, etc.) during reaction, thereby producing zerovalent nickel complexes.

The aforementioned zerovalent nickel complexes and zerovalent nickel complexes produced from divalent nickel complexes during reaction may be converted into zerovalent nickel complexes that are involved in reaction by acting on the ligand added during the reaction as necessary. The number of ligands coordinated to a zerovalent nickel complex during reaction is not necessarily known. The nickel complexes preferably have a high capability to stabilize the zerovalent nickel complex produced in the system. Preferable examples thereof include complexes having phosphine, diamine, bipyridyl, in particular, phosphine, or the like, as a ligand.

Preferable examples of phosphines include trialkylphosphine and triarylphosphine. Examples of trialkylphosphine include tri(C3-20 alkyl)phosphine such as tricyclohexylphosphine, triisopropylphosphine, tri-t-butylphosphine, trithexylphosphine, triadamantylphosphine, tricyclopentylphosphine, di-t-butylmethylphosphine, tribicyclo[2,2,2]octylphosphine, and trinorbornylphosphine. Examples of triarylphosphine include tri(monocyclic aryl)phosphine such as triphenylphosphine, trimesitylphosphine, and tri(o-tolyl)phosphine. Among these, triphenylphosphine, tricyclohexylphosphine, and triisopropylphosphine are preferable.

Examples of diamines include tetramethylethylenediamine, 1,2-diphenylethylenediamine, and the like.

Among these ligands, bulky ligands such as triarylphosphine, such as triphenylphosphine and tri(o-tolyl)phosphine, and tricyclohexylphosphine are preferable. Generally, it is possible to more efficiently obtain the target substituted fluoroolefin by using a nickel complex having a bulky ligand, such as triarylphosphine.

Among these catalysts, palladium-containing catalysts, palladium complexes, in particular, zerovalent palladium phosphine complexes (in particular, triphenylphosphinecomplexo) are preferable in terms of the reactivity, yield, selectivity, and the like of the target fluoroolefin substituted with an organic group.

The amount of the palladium or nickel catalysts (or palladium or nickel complexes) is not particularly limited. However, the amount of the zerovalent or divalent palladium or nickel complexes added as a reagent is generally about 0.001 to 1 mol, preferably about 0.01 to 0.2 mol, per mol of the organic magnesium compound.

When a ligand is added, the amount of the ligand is generally about 0.002 to 2 mol, preferably about 0.02 to 0.4 mol, per mol of the organic magnesium compound. The molar ratio of the ligand to the catalyst is generally 2/1 to 10/1, preferably 2/1 to 4/1.

The organic magnesium compound used in the method of the present invention is a compound containing an organic group that can replace a fluorine atom or atoms of the $sp^2$ hybridized carbon atom of the fluoroolefin; the compound serves as a nucleophilic reagent.

Typical examples of organic magnesium compounds include the compounds represented by Formula (7a) and/or Formula (7b):

$$RMgX \tag{7a}$$

$$R_2Mg \tag{7b}$$

wherein R is substituted or unsubstituted aryl or alkyl, X is Cl, Br, or I.

These compounds may form a solvate with the solvent in the reaction system.

Examples of substituted or unsubstituted aryl represented by R include mono-, di-, or tri-cyclic aryl such as phenyl, naphthyl, anthracenyl, and phenanthryl. Examples of the substituents of aryl include lower (in particular, C1-6) alkyl such as methyl, ethyl, n-propyl, isopropyl, n-butyl, and n-hexyl; lower (in particular, C26) alkenyl such as vinyl, allyl and crotyl; lower (in particular, C16) alkoxy such as methoxy, ethoxy, n-propoxy, isopropoxy and n-butoxy; and aryl such as phenyl and naphthyl. The aryl may have 1 to 4 (in particular, 1 to 2) of the aforementioned substituents. R is preferably phenyl.

Examples of substituted or unsubstituted alkyl represented by R include lower (in particular, C1-6) alkyl such as methyl, ethyl, n-propyl, isopropyl, n-butyl, and n-hexyl. Examples of the substituents of alkyl include (in particular, C1-6) alkoxy such as methoxy, ethoxy, n-propoxy, isopropoxy, and n-butoxy; and aryl such as phenyl and naphthyl. The alkyl may have 1 to 3 (in particular, 1 to 2) of the aforementioned substituents.

X is preferably Br or Cl.

As the organic magnesium compound, a Grignard reagent obtained by reacting organohalide and magnesium metal (Mg) in an inactive solvent such as THF can be generally used. In particular, the magnesium compound represented by Formula (7b) may be prepared by adding a poor solvent to the solution of Grignard reagent, filtering the mixture to separate precipitated insoluble salt (e.g., $MgX_2$), and drying the filtrate as required. These steps may be performed according to known methods.

The amounts of the fluoroolefin and the organic magnesium compound may be appropriately determined according to the number of fluorine atoms subjected to substitution reaction in the fluoroolefin. Generally, the amount of the fluoroolefin is about 0.1 to 100 mol, preferably about 0.5 to 10 mol, per mol of the organic magnesium compound.

In the method of the present invention, a fluorophilic compound is further added to the reaction system and/or the reaction is performed by heating the reaction system so as to facilitate the reaction between the reaction intermediate (n complex) represented by Formula (1) and the reaction intermediate (σ complex) represented by Formula (2), thereby more easily causing the oxidative addition reaction with respect to the C—F bond. This facilitates the catalytic reaction.

Examples of the fluorophilic compound include Lewis acidic metal halides formed of a halogen atom and a metal (hard metal) having affinity with fluorine atom. Examples thereof include lithium halide, magnesium halide, and zinc halide. More specifically, examples include lithium halides such as lithium chloride, lithium bromide, and lithium iodide; magnesium halides such as magnesium bromide, and magnesium iodide; and zinc halides such as zinc chloride, zinc bromide, and zinc iodide. Lithium halides such as lithium iodide are preferable.

When a fluorophilic compound is added, the amount thereof is generally about 0.5 to 10 mol, preferably about 1 to 1.5 mol, per mol of the organic magnesium reagent.

The reaction temperature is not particularly limited. Generally, the reaction temperature is −100° C. to 200° C., preferably 0° C. to 150° C., more preferably room temperature (about 20° C.) to 100° C. In view of facilitation of oxidative addition reaction of the nickel or palladium catalyst with respect to the C—F bond, the heating is performed at 40° C. to 150° C., preferably 50° C. to 100° C. Because the trifluorovinyl derivative, i.e., the reaction product, may dimerize under a high temperature, the upper limit of the reaction temperature may be determined to be less than the temperature causing dimerization.

Although it is not particularly limited, the reaction time is about 10 minutes to 72 hours.

Although it is not particularly limited, the reaction is generally performed in the presence of inactive gas, such as argon or nitrogen, considering the activity of the catalyst including nickel or palladium. Further, the reaction may be performed under increased pressure, atmospheric pressure, or decreased pressure. Generally, the reaction is preferably performed under increased pressure, i.e., at about 0.1 to 10 MPa, more preferably about 0.1 to 1 MPa.

The solvent to be used in the above method is not limited insofar as it does not adversely affect the reaction. Examples thereof include aromatic hydrocarbons solvents such as benzene, toluene, and xylene; aliphatic hydrocarbons solvents such as hexane and cyclohexane; and ether solvents such as tetrahydrofuran (THF), dioxane, diethyl ether, glyme, and diglyme. Of these, benzene, toluene, diethyl ether, dioxane, THF and the like are preferable. THF is particularly preferable.

The method of the present invention enables reaction by simultaneously mixing a catalyst including nickel or palladium, a fluoroolefin, and an organic magnesium compound. The reaction may otherwise be performed first by preparing or separating a nickel or palladium fluorine-containing vinyl complex from a catalyst including nickel or palladium and a fluoroolefin, and then reacting the fluoroolefin and the organic magnesium compound using the complex.

A typical example of the present invention using TFE as a raw material is described below.

The compound (1-substitution product and/or 1,1-disubstitution product) represented by Formula (4) and/or (5) can be produced by reacting TFE and an organic magnesium compound in the presence of a catalyst comprising nickel or palladium. The above reaction conditions may be used for this reaction.

[Chem. 6]

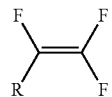

(4)

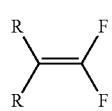

(5)

wherein R is the same as above.

The compound (1,1-disubstitution product) represented by Formula (5') can be produced by (i) reacting TFE and an organic magnesium compound in the presence of a catalyst comprising nickel or palladium, thereby producing the compound represented by Formula (4), and (ii) further reacting the compound represented by Formula (4) and an organic magnesium compound in the presence of a catalyst comprising nickel or palladium.

[Chem. 7]

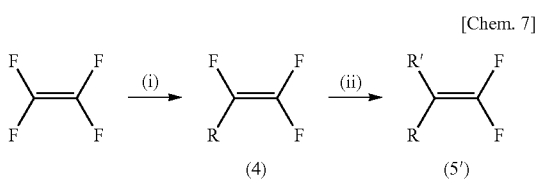

wherein, R and R' are the same or different, and each represents substituted or unsubstituted aryl or alkyl.

The organic magnesium compound used in Steps (i) and (ii) may be the same or different. More specifically, examples of the organic magnesium compound used in Step (i) include the compounds represented by the aforementioned Formula (7a) and Formula (7b). Examples of the organic magnesium compound used in Step (ii) include the compounds represented by Formula (7a') and Formula (7b') below:

R'MgX'  (7a')

R'$_2$Mg  (7b')

wherein X' represents Cl, Br or I, R' is the same as above, and R and R' are the same or different.

Further, the reaction conditions in Step (i) and (ii) may be the same or different, and are also not particularly limited insofar as the desired product can be obtained.

The present invention encompasses both the case of first obtaining the compound represented by Formula (4) in Step (i) and then subjecting the obtained compound to Step (ii) to produce the compound of Formula (5'), and the case of performing Steps (i) and (ii) as one-pot synthesis starting from TFE.

This is advantageous because a variety of compounds of Formula (5') can be produced, in particular, wherein R and R' are different.

Furthermore, the method of the present invention easily produces 1-substituted fluoroolefin, 1,1-disubstituted fluoroolefin or the like from a fluoroolefin such as readily available TFE. The present invention is particularly characteristic in terms of its easy production of 1,1-disubstituted fluoroolefin. For example, the addition elimination reaction of TFE with two molecules of an alkyl metal reagent, as in Non-Patent Document 4, only produces 1,2-disubstituted fluoroolefin, and cannot produce 1,1-disubstituted fluoroolefin. In contrast, the method of the present invention is more advantageous in terms of its production of 1,1-disubstituted fluoroolefin from 1,1-difluoroolefin such as TFE.

Another typical example of the present invention using trifluoroethylene as a raw material is described below.

The compound represented by Formula (4a) can be produced by reacting trifluoroethylene and an organic magnesium compound in the presence of a catalyst containing nickel or palladium. The above reaction conditions may be used for this reaction.

[Chem. 8]

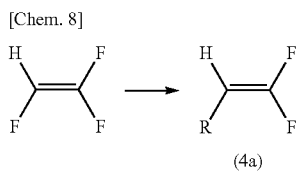

wherein R is the same as above.

In this reaction, only the compound represented by Formula (4a) is produced from trifluoroethylene. That is, the reaction does not substitute other fluorine atoms. This is also an advantage in using the transition metal catalyst and the organic magnesium reagent of the present invention. At present, a very few methods have been reported as a synthesis method of the compound represented by Formula (4a). As such, the method of the present invention is useful for the production of the compound represented by Formula (4a).

The thus-obtained substituted fluoroolefin is useful for, for example, fluorocarbon rubber, materials for antireflection film, ion-exchange membranes, fuel-cell electrolytes, liquid crystal materials, materials for piezoelectric elements, enzyme inhibitors, materials for insecticide and the like.

EXAMPLES

The present invention is described below with reference to examples; these examples, however, do not limit the scope of the invention.

The abbreviations used in the Examples are as follows.
cod: cyclooctadiene
Cy: cyclohexyl
TFE: tetrafluoroethylene
THF: tetrahydrofuran
PhMgBr: phenyl magnesium bromide
dba: dibenzylideneacetone Example 1

In a glove box, a THF (0.4 ml) solution of Ni(cod)$_2$ (5.5 mg, 0.02 mmol) and PPh$_3$ (10.6 mg, 0.04 mmol) was prepared in a pressure tube (capacity=2 ml, the same hereinafter). A PhMgBr ether solution (3 M, 0.067 ml, 0.2 mmol) and α,α,α-trifluorotoluene (14 μL, 0.114 mmol: internal standard for the $^{19}$F-NMR measurement) were added to the solution. TFE (0.313 mmol: calculated from the container capacity of 2 ml and the applied pressure of 0.35 MPa) was further added to the mixture. This reaction solution was allowed to stand for 8 hours at room temperature (20° C., the same hereinafter). The reaction was monitored by $^{19}$F-NMR, and it was confirmed based on the internal standard that α,β,β-trifluorostyrene, 1,1-difluoro-2,2-diphenylethylene, and 1,2-difluoro-1,2-diphenylethylene were obtained at yields of 49%, 58%, 5%, respectively.

α,β,β-trifluorostyren $^1$H-NMR (C$_6$D$_6$): δ 7.16 (tt, J=7.5, 1.5 Hz, 1H), 7.47 (dd, J=8.5, 7.5 Hz, 2H), 7.59 (dd, J=8.5, 1.5 Hz, 2H).
$^{19}$F-NMR (C$_6$D$_6$): δ−103.5 (dd, J=72, 32 Hz, 1F), −118.0 (dd, J=72, 107 Hz, 1F), −179.2 (dd, J=107, 32 Hz, 1F).

1,1-difluoro-2,2-diphenylethylene $^{19}$F-NMR (C$_6$D$_6$): δ−91.5 (s). MS m/z 216 (M+), 166 (M-CF$_2$), 50 (CF$_2$).

1,2-difluoro-1,2-diphenylethylene $^{19}$F-NMR (C$_6$D$_6$): δ trans isomer −154.8 (s), cis isomer −130.5 (s).

Example 2

In a glove box, a THF (0.4 ml) solution of Ni(cod)$_2$ (5.5 mg, 0.02 mmol) and PPh$_3$ (10.6 mg, 0.04 mmol) was prepared in a pressure tube. A PhMgBr ether solution (3 M, 0.133 ml, 0.4 mmol) and α,α,α-trifluorotoluene (14 μL: internal standard for the $^{19}$F-NMR measurement) were added to the solution. TFE (0.313 mmol: introduced until the pressure reached 0.35 MPa) was further added to the mixture. This reaction solution was allowed to stand for 48 hours at room temperature. The reaction was monitored by $^{19}$F-NMR, and it was confirmed based on the internal standard that α,β,β-trifluorostyrene, 1,1-difluoro-2,2-diphenylethylene, and 1,2-difluoro-1,2-diphenylethylene were obtained at yields of 43%, 26%, and 6%, respectively.

Example 3

In a glove box, a THF (0.4 ml)/$C_6D_6$ (0.1 ml) solution of $Pd_2(dba)_3$ (5 mg, 0.005 mmol), $PPh_3$ (5.3 mg, 0.02 mmol) and LiI (16.1 mg, 0.12 mmol) was prepared in a pressure tube. A PhMgBr ether solution (3 M, 0.038 ml, 0.115 mmol) and α,α,α-trifluorotoluene (14 μL: internal standard for the $^{19}$F-NMR measurement) were added to the solution. TFE (0.313 mmol: introduced until the pressure reached 0.35 MPa) was further added to the mixture. This reaction solution was heated for 2 hours at 60° C. The reaction was monitored by $^{19}$F-NMR, and it was confirmed based on the internal standard that α,β,β-trifluorostyrene and 1,1-difluoro-2,2-diphenylethylene were obtained at yields of 49% and 15%, respectively.

Example 4

In a glove box, a THF (0.4 ml)/$C_6D_6$ (0.1 ml) solution of $Pd_2(dba)_3$ (5 mg, 0.005 mmol), $PCy_3$ (5.6 mg, 0.02 mmol) and LiI (16.1 mg, 0.12 mmol) was prepared in a pressure tube. A PhMgBr ether solution (3 M, 0.038 ml, 0.115 mmol) and α,α,α-trifluorotoluene (14 μL: internal standard for the $^{19}$F-NMR measurement) were added to the solution. TFE (0.313 mmol: introduced until the pressure reached 0.35 MPa) was further added to the mixture. This reaction solution was heated for 2 hours at 60° C. The reaction was monitored by $^{19}$F-NMR, and it was confirmed based on the internal standard that α,β,β-trifluorostyrene, 1,1-difluoro-2,2-diphenylethylene, and 1,2-difluoro-1,2-diphenylethylene were obtained at yields of 18%, 6%, and 6%, respectively.

Reference Example 1

$Ph_2Mg$ $(THF)_2$: Preparation of Diphenyl Magnesium THF Complex 1,4-dioxane was added to a THF solution (1 M, purchased from Aldrich) of PhMgBr, thereby precipitating $MgBr_2$. The dropwise addition of 1,4-dioxane was finished when the precipitation of $MgBr_2$ stopped. The precipitated $MgBr_2$ was removed by filtration inside the glove box, and the filtrate containing the target substance was dried to obtain $Ph_2Mg(THF)_2$. The obtained $Ph_2Mg(THF)_2$ was hermetically sealed in a glass container and was kept in a glove box.

Example 5

In a glove box, a $C_6D_6$ (0.5 ml) solution of $Pd_2(dba)_3$ (5 mg, 0.005 mmol), $PPh_3$ (5.3 mg, 0.02 mmol), LiI (16.1 mg, 0.12 mmol), $Ph_2Mg(THF)_2$ (37.1 mg, 0.115 mmol) was prepared in a pressure tube. α,α,α-trifluorotoluene (14 μL: internal standard for the $^{19}$F-NMR measurement) was added to the solution. TFE (0.313 mmol: introduced until the pressure reached 0.35 MPa) was further added to the mixture. This reaction solution was allowed to stand for 72 hours at room temperature. The reaction was observed by $^{19}$F-NMR, and it was confirmed that α,β,β-trifluorostyrene, 1,1-difluoro-2,2-diphenylethylene, and 1,2-difluoro-1,2-diphenylethylene were obtained at yields of 21% (based on the number of moles of $Ph_2Mg(THF)_2$ used for the reaction), 10%, and 2%, respectively.

Example 6

In a glove box, a THF (0.4 ml)/$C_6D_6$ (0.1 ml) solution of $Pd_2(dba)_3$ (5 mg, 0.005 mmol), $PPh_3$ (5.3 mg, 0.02 mmol), LiI (16.1 mg, 0.12 mmol), $Ph_2Mg(THF)_2$ (37.1 mg, 0.115 mmol) was prepared in a pressure tube. α,α,α-trifluorotoluene (14 μL: internal standard for the $^{19}$F-NMR measurement) was added to the solution. TFE (0.313 mmol: introduced until the pressure reached 0.35 MPa) was further added to the mixture. This reaction solution was allowed to stand for 27 hours at room temperature. The reaction was monitored by $^{19}$F-NMR, and it was confirmed that α,β,β-trifluorostyrene, 1,1-difluoro-2,2-diphenylethylene, and 1,2-difluoro-1,2-diphenylethylene were obtained at yields of 86% (based on the number of moles of $Ph_2Mg(THF)_2$ used for the reaction), 2%, and 4%, respectively.

Reference Example 2

A $C_6D_6$-THF-$d_8$ (1:1, 0.5 mL) solution of $Ph_2Mg(THF)_2$ (22.6 mg, 0.07 mmol) was prepared in a pressure tube, and TFE (0.313 mmol: introduced until the pressure reached 0.35 MPa) was added to the solution. The reaction solution was allowed to stand at room temperature while being monitored by $^1$H-NMR. The inversion rate of $Ph_2Mg(THF)_2$ was estimated from the integration ratio of proton, which was based on the β hydrogen of THF present in a reaction system.

The inversion rate was 3% when the reaction time was 15 minutes, 62% when the reaction time was 5 hours, and 89% when the reaction time was 12 hours.

Example 7

A $C_6D_6$-THF-$d_8$ (1:1, 0.5 mL) solution of $Ni(cod)_2$ (2.6 mg, 0.01 mmol) and $PPh_3$ (5.3 mg, 0.02 mmol) was prepared in a pressure tube, and $Ph_2Mg(THF)_2$ (32.2 mg, 0.10 mmol) was added to the solution. TFE (0.313 mmol: introduced until the pressure reached 0.35 MPa) was further added to the mixture. As in Reference Example 2, the reaction was tracked by $^1$H-NMR.

The inversion rate was 95% when the reaction time was 15 minutes and 99% when the reaction time was 1 hour.

According to Example 7 and Reference Example 2, it was found that the substitution reaction of TFE advanced very easily when a nickel complex was added as a catalyst.

Example 8

Synthesis of 1,1-difluoro-2-phenylethylene from trifluoroethylene

A THF-$d_8$ (0.5 ml) solution of trifluoroethylene (0.313 mmol), $Ni(cod)_2$ (2.6 mg, 0.01 mmol), $PPh_3$ (5.3 mg, 0.02 mmol), and $Ph_2Mg(THF)_2$ (32.2 mg, 0.10 mmol) was prepared in a pressure tube and was allowed to stand at 60° C. The reaction was monitored by $^{19}$F-NMR, and the production of 1,1-difluoro-2-phenylethylene was confirmed. The rest was the trifluorostyrene used as a raw material. The product in which the fluorine of the difluoromethylene (CF$_2$=) of the trifluorostyrene is substituted was not detected.

1,1-difluoro-2-phenylethylene $^{19}$F-NMR (THF-d$_8$): δ−86.5 (dd, J=37.0, 29.2 Hz, 1F), −83.4 (dd, J=37.0, 4.4 Hz, 1F).

Example 9

In a glove box, a THF (0.4 ml)/C$_6$D$_6$ (0.1 ml) solution of Pd$_2$(dba)$_3$ (5 mg, 0.005 mmol) and PPh$_3$ (5.3 mg, 0.02 mmol) was prepared in a pressure tube. An MeMgBr ether solution (3 M, 0.033 ml, 0.100 mmol) and α,α,α-trifluorotoluene (12.3 μL, 0.100 mmol: internal standard for the $^{19}$F-NMR measurement) were added to the solution. TFE (0.313 mmol: introduced until the pressure reached 0.35 MPa) was further added to the mixture. This reaction solution was heated for 2 hours at 60° C. The reaction was observed by $^{19}$F-NMR, and it was confirmed based on the internal standard that 1,1,2-trifluoro-1-propene and 1,1-difluoro-2-methyl-1-propene were obtained.

1,1,2-trifluoro-1-propene $^{19}$F-NMR (C$_6$D$_6$-THF-d$_8$): δ−109.8 (ddq, 1F), −129.4 (ddq, 1F), −170.2 (m, 1F).

1,1-difluoro-2-methyl-1-propene $^{19}$F-NMR (C$_6$D$_6$-THF-d$_8$): δ−98.41 (septet, J=3.1 Hz).
$^{1}$H-NMR (C$_6$D$_6$-THF-d$_8$): δ 1.56 (d, J=3.1 Hz).

Example 10

Synthesis of α,β,β-trifluorostyrene

A catalytic reaction was performed while observing the $^{19}$F-NMR spectra using a pressure NMR tube (Wilmad-Lab-Glass, 524-PV-7). A THF-d$_8$/THF solution (0.4 ml; volume ratio=3/1) was added to a solid mixture of ZnCl$_2$ (13.6 mg, 0.100 mmol) and LiI (32.1 mg, 0.240 mmol). A THF solution (2.0 M, 0.100 ml, 0.200 mmol) of PhMgBr, a THF solution (0.5 mM, 20.0 μL, 1.0×10$^{-5}$ mmol) of Pd$_2$(dba)$_3$, and α,α,α-trifluorotoluene (12.3 μL, 0.100 mmol: internal standard for the $^{19}$F-NMR measurement) were added to the resulting solution. The obtained solution was transferred to an NMR tube. After degassing, TFE (3.5 atm, 0.313 mmol) was introduced into the NMR tube. The reaction mixture was kept at 40° C. until the reaction was completed (4 hours). The reaction was observed by $^{19}$F-NMR, and it was confirmed that α,β,β-trifluorostyrene was obtained at a yield of 145% (based on the number of moles of the zinc reagent used for the reaction).

α,β,β-trifluorostyrene $^{19}$F-NMR (372 MHz, in THF/THF-d$_8$, rt, δ/ppm): −179.0 (dd, J$_{FF}$=32.7, 110.3 Hz, 1F, F$^1$), −118.5 (dd, J$_{FF}$=73.5, 110.3 Hz, 1F, F$^3$), −104.2 (dd, J$_{FF}$=32.7, 73.5 Hz, 1F, F$^2$).

Example 11

Synthesis of α,β,β-trifluorostyrene

A catalytic reaction was performed while observing the $^{19}$F-NMR spectra using a pressure NMR tube (Wilmad-Lab-Glass, 524-PV-7). A THF-d$_8$/THF solution (0.4 ml; volume ratio=3/1) was added to a solid mixture of ZnCl$_2$ (13.6 mg, 0.100 mmol) and LiI (32.1 mg, 0.240 mmol). A THF solution (2.0 M, 0.100 ml, 0.200 mmol) of PhMgCl, a THF solution (0.5 mM, 20.0 μL, 1.0×10$^{-5}$ mmol) of Pd$_2$(dba)$_3$, and α,α,α-trifluorotoluene (12.3 μL, 0.100 mmol: internal standard for the $^{19}$F-NMR measurement) were added to the resulting solution. The obtained solution was transferred to an NMR tube. After degassing, TFE (3.5 atm, 0.313 mmol) was introduced into the NMR tube. The reaction mixture was kept at 40° C. until the reaction was completed (2 hours). The reaction was observed by $^{19}$F-NMR, and it was confirmed that α,β,β-trifluorostyrene was obtained at a yield of 162% (based on the number of moles of the zinc reagent used for the reaction).

Example 12

Synthesis of 1-methyl-4-(1,2,2-trifluoroethenyl)benzene

A catalytic reaction was performed while observing the $^{19}$F-NMR spectra using a pressure NMR tube (Wilmad-Lab-Glass, 524-PV-7). A THF-d$_8$/THF solution (0.4 ml; volume ratio=3/1) was added to a solid mixture of ZnCl$_2$ (13.6 mg, 0.100 mmol) and LiI (32.1 mg, 0.240 mmol). A THF solution (1.0 M, 0.200 ml, 0.200 mmol) of p-Me-C6H4—MgBr, a THF solution (0.5 mM, 20.0 μL, 1.0×10$^{-5}$ mmol) of Pd$_2$(dba)$_3$, and α,α,α-trifluorotoluene (12.3 μL, 0.100 mmol: internal standard for the $^{19}$F-NMR measurement) were added to the resulting solution. The obtained solution was transferred to an NMR tube. After degassing, TFE (3.5 atm, 0.313 mmol) was introduced into the NMR tube. The reaction mixture was kept at 40° C. until the reaction was completed (6 hours). The reaction was observed by $^{19}$F-NMR, and it was confirmed that 1-methyl-4-(1,2,2-trifluoroethenyl)benzene was obtained at a yield of 150% (based on the number of moles of the zinc reagent used for the reaction).

1-methyl-4-(1,2,2-trifluoroethenyl)benzene $^{1}$F-NMR (372 MHz, in THF/THF-d$_8$, rt, δ/ppm): −178.6 (dd, J$_{FF}$=32.0, 109.3 Hz, 1F, F$^1$), −119.4 (dd, J$_{FF}$=76.0, 109.3 Hz, 1F, F$^3$), −105.2 (dd, J$_{FF}$=32.0, 76.0 Hz, 1F, F$^2$).

Example 13

Synthesis of 1-methyl-3-(1,2,2-trifluoroethenyl)benzene

A catalytic reaction was performed while observing the $^{19}$F-NMR spectra using a pressure NMR tube (Wilmad-Lab-Glass, 524-PV-7). A THF-d$_8$/THF solution (0.4 ml; volume ratio=3/1) was added to a solid mixture of ZnCl$_2$ (13.6 mg, 0.100 mmol) and LiI (32.1 mg, 0.240 mmol). A THF solution (1.0 M, 0.200 ml, 0.200 mmol) of m-Me-C$_6$H$_4$—MgCl, a THF solution (0.5 mM, 20.0 μL, 1.0×10$^{-5}$ mmol) of Pd$_2$(dba)$_3$, and α,α,α-trifluorotoluene (12.3 μL, 0.100 mmol: internal standard for the $^{19}$F-NMR measurement) were added to the resulting solution. The obtained solution was transferred to an NMR tube. After degassing, TFE (3.5 atm, 0.313 mmol) was introduced into the NMR tube. The reaction mixture was kept at 40° C. until the reaction was completed (4 hours). The reaction was observed by $^{19}$F-NMR, and it was confirmed that 1-methyl-3-(1,2,2-trifluoroethenyl)benzene was obtained at a yield of 144% (based on the number of moles of the zinc reagent used for the reaction).

1-methyl-3-(1,2,2-trifluoroethenyl)benzene $^{19}$F-NMR (372 MHz, in THF/THF-d$_8$, rt, δ/ppm): −178.7 (dd, J$_{FF}$=31.9, 109.3 Hz, 1F, F$^1$), −118.6 (dd, J$_{FF}$=74.0, 109.3 Hz, 1F, F$^3$), −104.4 (dd, J$_{FF}$=31.9, 74.0 Hz, 1F, F$^2$).

Example 14

Synthesis of
1-methyl-2-(1,2,2-trifluoroethenyl)benzene

A catalytic reaction was performed while observing the $^{19}$F-NMR spectra using a pressure NMR tube (Wilmad-Lab-Glass, 524-PV-7). A THF-d$_8$/THF solution (0.4 ml; volume ratio=3/1) was added to a solid mixture of ZnCl$_2$ (13.6 mg, 0.100 mmol) and LiI (32.1 mg, 0.240 mmol). A THF solution (1.0 M, 0.200 ml, 0.200 mmol) of o-Me-C$_6$H$_4$—MgCl, a THF solution (0.5 mM, 20.0 μL, 1.0×10$^{-5}$ mmol) of Pd$_2$(dba)$_3$, and α,α,α-trifluorotoluene (12.3 μL, 0.100 mmol: internal standard for the $^{19}$F-NMR measurement) were added to the resulting solution. The obtained solution was transferred to an NMR tube. After degassing, TFE (3.5 atm, 0.313 mmol) was introduced into the NMR tube. The reaction mixture was kept at 40° C. until the reaction was completed (8 hours). The reaction was observed by $^{19}$F-NMR, and it was confirmed that 1-methyl-2-(1,2,2-trifluoroethenyl)benzene was obtained at a yield of 113% (based on the number of moles of the zinc reagent used for the reaction).

1-methyl-2-(1,2,2-trifluoroethenyl)benzene $^{19}$F-NMR (372 MHz, in THF/THF-d$_8$, rt, δ/ppm): −163.8 (dd, J$_{FF}$=29.4, 117.1 Hz, 1F, F$^1$), −121.4 (dd, J$_{FF}$=77.6, 117.1 Hz, 1F, F$^3$), −107.1 (dd, J$_{FF}$=29.4, 77.6 Hz, 1F, F$^2$).

Isolation of
1-methyl-2-(1,2,2-trifluoroethenyl)benzene

THF (5.0 ml) was added to a solid mixture of ZnCl$_2$ (136 mg, 1.00 mmol) and LiI (321 mg, 2.40 mmol). A THF solution (1.0 M, 2.00 ml, 200 mmol) of o-Me-C$_6$H$_4$-MgCl and a THF solution (0.5 mM, 0.20 mL, 1.0×10$^{-4}$ mmol) of Pd$_2$(dba)$_3$ were added to the resulting solution. The obtained solution was transferred to an autoclave reactor. Thereafter, TFE (3.5 atm) was introduced into the reactor and the reaction mixture was kept at 40° C. for 8 hours. After removing unreacted TFE from the reactor, the reaction mixture was quenched with deionized water (20 mL). Thereafter, the aqueous phase was extracted 3 times using pentane (15 mL). Meanwhile, the organic phase was dried over MgSO$_4$. Pentane and THF were removed by distillation and 1-methyl-2-(1,2,2-trifluoroethenyl)benzene was obtained at an isolation yield of 33%.

1-methyl-2-(1,2,2-trifluoroethenyl)benzene $^1$H-NMR (400 MHz, C$_6$D$_6$, rt, δ/ppm): 2.07 (s, 3H, CH$_3$), 6.80-6.90 (m, 2H, C$_6$H$_4$), 6.92-7.00 (m, 1H, C$_6$H$_4$), 7.00-7.08 (m, 1H, C$_6$H$_4$).
$^{13}$C($^1$H)—NMR (100.6 MHz, C$_6$D$_6$, rt, δ/Ppm): 19.6 (s, CH$_3$), 126.3 (s, C$^4$), 126.4 (dd, J$_{CF}$=19.2, 4.6 Hz, C$^2$), 128.6 (ddd, J$_{CF}$=233.3, 51.4, 19.1 Hz, —CF═CF$_2$), 130.3 (apparent dd, J$_{CF}$=3.1, 2.3 Hz, C$^3$), 130.3 (d, J$_{CF}$=2.3 Hz, C$^5$), 131.1 (s, C$^6$), 138.7 (d, J$_{CF}$=3.1 Hz, C$^1$), 154.1 (ddd, J$_{CF}$=306.7, 292.9, 54.5 Hz, —CF═CF$_2$).

Example 15

Synthesis of
1-methoxy-4-(1,2,2-trifluoroethenyl)benzene

A catalytic reaction was performed while observing the $^{19}$F-NMR spectra using a pressure NMR tube (Wilmad-Lab-Glass, 524-PV-7). A THF-d$_8$/THF solution (0.4 ml; volume ratio=3/1) was added to a solid mixture of ZnCl$_2$ (13.6 mg, 0.100 mmol) and LiI (32.1 mg, 0.240 mmol). A THF solution (0.5 M, 0.400 ml, 0.200 mmol) of p-MeO—C$_6$H$_4$—MgBr, a THF solution (0.5 mM, 20.0 μL, 1.0×10$^{-5}$ mmol) of Pd$_2$(dba)$_3$, and α,α,α-trifluorotoluene (12.3 μL, 0.100 mmol: internal standard for the $^{19}$F-NMR measurement) were added to the resulting solution. The obtained solution was transferred to an NMR tube. After degassing, TFE (3.5 atm, 0.313 mmol) was introduced into the NMR tube. The reaction mixture was kept at 40° C. until the reaction was completed (2.5 hours). The reaction was observed by $^{19}$F-NMR, and it was confirmed that 1-methoxy-4-(1,2,2-trifluoroethenyl)benzene was obtained at a yield of 126% (based on the number of moles of the zinc reagent used for the reaction).

1-methoxy-4-(1,2,2-trifluoroethenyl)benzene $^{19}$F-NMR (372 MHz, in THF/THF-d$_3$, rt, δ/ppm): −177.2 (dd, J$_{FF}$=31.2, 110.3 Hz, 1F, F$^1$), −121.2 (dd, J$_{FF}$=79.1, 110.3 Hz, 1F, F$^3$), −106.7 (dd, J$_{FF}$=31.2, 79.1 Hz, 1F, F$^2$).

Example 16

Synthesis of
1-fluoro-4-(1,2,2-trifluoroethenyl)benzene

A catalytic reaction was performed while observing the $^{19}$F-NMR spectra using a pressure NMR tube (Wilmad-Lab-Glass, 524-PV-7). A THF-d$_8$/THF solution (0.4 ml; volume ratio=3/1) was added to a solid mixture of ZnCl$_2$ (13.6 mg, 0.100 mmol) and LiI (32.1 mg, 0.240 mmol). A THF solution (1.0 M, 0.200 ml, 0.200 mmol) of p-F—C$_6$H$_4$—MgBr, a THF solution (0.5 mM, 20.0 μL, 1.0×10$^{-5}$ mmol) of Pd$_2$(dba)$_3$, and α,α,α-trifluorotoluene (12.3 μL, 0.100 mmol: internal standard for the $^{19}$F-NMR measurement) were added to the resulting solution. The obtained solution was transferred to an NMR tube. After degassing, TFE (3.5 atm, 0.313 mmol) was introduced into the NMR tube. The reaction mixture was kept at 40° C. until the reaction was completed (4 hours). The reaction was observed by $^{19}$F-NMR, and it was confirmed that 1-fluoro-4-(1,2,2-trifluoroethenyl)benzene was obtained at a yield of 110% (based on the number of moles of the zinc reagent used for the reaction).

1-fluoro-4-(1,2,2-trifluoroethenyl)benzene $^{19}$F-NMR (372 MHz, in THF/THF-d$_8$, rt, δ/ppm): −177.8 (dd, J$_{FF}$=31.2, 110.3 Hz, 1F, F$^1$), −119.0 (dd, J$_{FF}$=74.9, 110.3 Hz, 1F, F$^3$), −114.2 (br d, J$_{HF}$=4.1 Hz, 1F, C$_8$H$_4$F), −104.6 (ddd, J$_{HF}$=4.1 Hz, J$_{FF}$=31.2, 74.9 Hz, 1F, F$^2$).

Example 17

Synthesis of
1-ethenyl-4-(1,2,2-trifluoroethenyl)benzene

A catalytic reaction was performed while observing the $^{19}$F-NMR spectra using a pressure NMR tube (Wilmad-Lab-Glass, 524-PV-7). A THF-d$_8$/THF solution (0.4 ml; volume ratio=3/1) was added to a solid mixture of ZnCl$_2$ (13.6 mg, 0.100 mmol) and LiI (32.1 mg, 0.240 mmol). A THF solution (0.71 M, 0.282 ml, 0.200 mmol) of (4-styly1)-MgBr, a THF solution (0.5 mM, 20.0 μL, 1.0×10$^{-5}$ mmol) of Pd$_2$(dba)$_3$, and α,α,α-trifluorotoluene (12.3 μL, 0.100 mmol: internal standard for the $^{19}$F-NMR measurement) were added to the resulting solution. The obtained solution was transferred to an NMR tube. After degassing, TFE (3.5 atm, 0.313 mmol) was introduced into the NMR tube. The reaction mixture was kept at 40° C. until the reaction was completed (4 hours). The reaction was observed by $^{19}$F-NMR, and it was confirmed that 1-ethenyl-4-(1,2,2-trifluoroethenyl)benzene was obtained at a yield of 129% (based on the number of moles of the zinc reagent used for the reaction).

1-ethenyl-4-(1,2,2-trifluoroethenyl)benzene $^{19}$F-NMR (372 MHz, in THF/THF-d$_8$, rt, δ/ppm): −179.2 (dd, J$_{FF}$=32.8, 110.3 Hz, 1F, F$^1$), −118.0 (dd, J$_{FF}$=72.3, 110.3 Hz, 1F, F$^3$), −103.9 (dd, J$_{FF}$=32.8, 72.3 Hz, 1F, F$^2$).

Example 18

Synthesis of 1-trifluoromethyl-4-(1,2,2-trifluoroethenyl)benzene

A catalytic reaction was performed while observing the $^{19}$F-NMR spectra using a pressure NMR tube (Wilmad-Lab-Glass, 524-PV-7). A THF-d$_8$/THF solution (0.4 ml; volume ratio=3/1) was added to a solid mixture of ZnCl$_2$ (13.6 mg, 0.100 mmol) and LiI (32.1 mg, 0.240 mmol). A THF solution (0.42 M, 0.476 ml, 0.200 mmol) of p-CF$_3$—MgBr, a THF solution (0.5 mM, 20.0 μL, 1.0×10$^{-5}$ mmol) of Pd$_2$(dba)$_3$, and α,α,α-trifluorotoluene (12.3 μL, 0.100 mmol: internal standard for the $^{19}$F-NMR measurement) were added to the resulting solution. The obtained solution was transferred to an NMR tube. After degassing, TFE (3.5 atm, 0.313 mmol) was introduced into the NMR tube. The reaction mixture was kept at 40° C. until the reaction was completed (18 hours). The reaction was observed by $^{19}$F-NMR, and it was confirmed that 1-trifluoromethyl-4-(1,2,2-trifluoroethenyl)benzene was obtained at a yield of 62% (based on the number of moles of the zinc reagent used for the reaction).

1-trifluoromethyl-4-(1,2,2-trifluoroethenyl)benzene $^{19}$F-NMR (372 MHz, in THF/THF-d$_8$, rt, δ/ppm): −179.8 (dd, J$_{FF}$=32.8, 109.2 Hz, 1F, F$^1$), −115.0 (dd, J$_{FF}$=65.5, 109.2 Hz, 1F, F$^3$), −100.8 (dd, J$_{FF}$=32.6, 65.1 Hz, 1F, F$^2$), −65.5 (s, 3F, CF$_3$).

Example 19

Synthesis of 1-methylthio 4-(1,2,2-trifluoroethenyl)benzene

A catalytic reaction was performed while observing the $^{19}$F-NMR spectra using a pressure NMR tube (Wilmad-Lab-Glass, 524-PV-7). A THF-d$_8$/THF solution (0.4 ml; volume ratio=3/1) was added to a solid mixture of ZnCl$_2$ (13.6 mg, 0.100 mmol) and LiI (32.1 mg, 0.240 mmol). A THF solution (0.5 M, 0.400 ml, 0.200 mmol) of p-MeS—MgBr, a THF solution (0.5 mM, 20.0 μL, 1.0×10$^{-5}$ mmol) of Pd$_2$(dba)$_3$, and α,α,α-trifluorotoluene (12.3 μL, 0.100 mmol: internal standard for the $^{19}$F-NMR measurement) were added to the resulting solution. The obtained solution was transferred to an NMR tube. After degassing, TFE (3.5 atm, 0.313 mmol) was introduced into the NMR tube. The reaction mixture was kept at 40° C. until the reaction was completed (21 hours). The reaction was observed by $^{19}$F-NMR, and it was confirmed that 1-methylthio 4-(1,2,2-trifluoroethenyl)benzene was obtained at a yield of 81% (based on the number of moles of the zinc reagent used for the reaction).

1-methylthio 4-(1,2,2-trifluoroethenyl)benzene $^{19}$F-NMR (372 MHz, in THF/THF-d$_8$, rt, δ/ppm): −178.8 (dd, J$_{FF}$=31.2, 109.2 Hz, 1F, F$^1$), −118.9 (dd, J$_{FF}$=74.9, 109.2 Hz, 1F, F$^3$), −104.8 (dd, J$_{FF}$=31.2, 74.9 Hz, 1F, F$^2$).

Example 20

Synthesis of 1-chloro-4-(1,2,2-trifluoroethenyl)benzene

A catalytic reaction was performed while observing the $^{19}$F-NMR spectra using a pressure NMR tube (Wilmad-Lab-Glass, 524-PV-7). A THF-d$_8$/THF solution (0.4 ml; volume ratio=3/1) was added to a solid mixture of ZnCl$_2$ (13.6 mg, 0.100 mmol) and LiI (32.1 mg, 0.240 mmol). An Et$_2$O solution (1.0 M, 0.200 ml, 0.200 mmol) of p-Cl—MgCl, a THF solution (0.5 mM, 20.0 μL, 1.0×10$^{-5}$ mmol) of Pd$_2$(dba)$_3$, and α,α,α-trifluorotoluene (12.3 μL, 0.100 mmol: internal standard for the $^{19}$F-NMR measurement) were added to the resulting solution. The obtained solution was transferred to an NMR tube. After degassing, TFE (3.5 atm, 0.313 mmol) was introduced into the NMR tube. The reaction mixture was kept at 40° C. until the reaction was completed (28 hours). The reaction was observed by $^{19}$F-NMR, and it was confirmed that 1-chloro-4-(1,2,2-trifluoroethenyl)benzene was obtained at a yield of 73% (based on the number of moles of the zinc reagent used for the reaction).

1-chloro-4-(1,2,2-trifluoroethenyl)benzene $^{19}$F-NMR (372 MHz, in THF/THF-d$_8$, rt, δ/ppm): −179.1 (dd, J$_{FF}$=32.8, 110.3 Hz, 1F, F$^1$), −117.2 (dd, J$_{FF}$=70.8, 110.3 Hz, 1F, F$^3$), −103.1 (dd, J$_{FF}$=32.8, 70.8 Hz, 1F, F$^2$).

Example 21

Synthesis of 1-(N,N-dimethylamino)-4-(1,2,2-trifluoroethenyl)benzene

A catalytic reaction was performed while observing the $^{19}$F-NMR spectra using a pressure NMR tube (Wilmad-Lab-Glass, 524-PV-7). A THF-d$_8$/THF solution (0.4 ml; volume ratio=3/1) was added to a solid mixture of ZnCl$_2$ (13.6 mg, 0.100 mmol) and LiI (32.1 mg, 0.240 mmol). A THF solution (0.5 M, 0.400 ml, 0.200 mmol) of p-Me$_2$N—MgBr, a THF solution (0.5 mM, 20.0 μL, 1.0×10$^{-5}$ mmol) of Pd$_2$(dba)$_3$, and α,α,α-trifluorotoluene (12.3 μL, 0.100 mmol: internal standard for the $^{19}$F-NMR measurement) were added to the resulting solution. The obtained solution was transferred to an NMR tube. After degassing, TFE (3.5 atm, 0.313 mmol) was introduced into the NMR tube. The reaction mixture was kept at 40° C. until the reaction was completed (2 hours). The reaction was observed by $^{19}$F-NMR, and it was confirmed that 1-(N,N-dimethylamino)-4-(1,2,2-trifluoroethenyl)benzene was obtained at a yield of 60% (based on the number of moles of the zinc reagent used for the reaction).

1-(N,N-dimethylamino)-4-(1,2,2-trifluoroethenyl) benzene $^{19}$F-NMR (372 MHz, in THF/THF-d$_8$, rt, δ/ppm): −176.1 (dd, J$_{FF}$=29.8, 110.3 Hz, 1F, F$^1$), −123.0 (dd, J$_{FF}$=85.2, 110.3 Hz, 1F, F$^3$), −108.6 (dd, J$_{FF}$=29.8, 85.2 Hz, 1F, F$^2$).

Example 22

Synthesis of 2-(1,2,2-trifluoroethenyl) naphthalene

A catalytic reaction was performed while observing the $^{19}$F-NMR spectra using a pressure NMR tube (Wilmad-Lab-Glass, 524-PV-7). A THF-d$_8$/THF solution (0.4 ml; volume ratio=3/1) was added to a solid mixture of ZnCl$_2$ (13.6 mg, 0.100 mmol) and LiI (32.1 mg, 0.240 mmol). A THF solution (0.5 M, 0.400 ml, 0.200 mmol) of (2-naphthyl)MgBr, a THF solution (0.5 mM, 20.0 μL, 1.0×10$^{-5}$ mmol) of Pd$_2$(dba)$_3$, and α,α,α-trifluorotoluene (12.3 μL, 0.100 mmol: internal standard for the $^{19}$F-NMR measurement) were added to the resulting solution. The obtained solution was transferred to an NMR tube. After degassing, TFE (3.5 atm, 0.313 mmol) was introduced into the NMR tube. The reaction mixture was kept at 40° C. until the reaction was completed (4 hours). The reaction was observed by $^{19}$F-NMR, and it was confirmed that 2-(1,2,2-trifluoroethenyl) naphthalene was obtained at a yield of 122% (based on the number of moles of the zinc reagent used for the reaction).

2-(1,2,2-trifluoroethenyl) naphthalene $^{19}$F-NMR (372 MHz, in THF/THF-d$_8$, rt, δ/ppm): −178.4 (dd, J$_{FF}$=32.0, 108.8 Hz, 1F, F$^1$), −118.0 (dd, J$_{FF}$=72.3, 108.8 Hz, 1F, F$^3$), −103.4 (dd, J$_{FF}$=31.0, 72.3 Hz, 1F, F$^2$).

Example 23

Synthesis of 2-(1,2,2-trifluoroethenyl) thiophene

A catalytic reaction was performed while observing the $^{19}$F-NMR spectra using a pressure NMR tube (Wilmad-Lab-Glass, 524-PV-7). A THF-d$_8$/THF solution (0.4 ml; volume ratio=3/1) was added to a solid mixture of ZnCl$_2$ (13.6 mg, 0.100 mmol) and LiI (32.1 mg, 0.240 mmol). A THF solution (1.0 M, 0.200 ml, 0.200 mmol) of (2-thienyl)MgBr, a THF solution (0.5 mM, 20.0 μL, 1.0×10$^{-5}$ mmol) of Pd$_2$(dba)$_3$, and α,α,α-trifluorotoluene (12.3 μL, 0.100 mmol: internal standard for the $^{19}$F-NMR measurement) were added to the resulting solution. The obtained solution was transferred to an NMR tube. After degassing, TFE (3.5 atm, 0.313 mmol) was introduced into the NMR tube. The reaction mixture was kept at 40° C. until the reaction was completed (75 hours). The reaction was observed by $^{19}$F-NMR, and it was confirmed that 2-(1,2,2-trifluoroethenyl) thiophene was obtained at a yield of 67% (based on the number of moles of the zinc reagent used for the reaction).

2-(1,2,2-trifluoroethenyl) thiophene $^{19}$F-NMR (372 MHz, in THF/THF-d$_8$, rt, δ/ppm): −171.9 (dd, J$_{FF}$=31.2, 110.3 Hz, 1F, F$^1$), −117.7 (dd, J$_{FF}$=72.3, 110.3 Hz, 1F, F$^3$), −106.5 (dd, J$_{FF}$=31.2, 72.3 Hz, 1F, F$^2$).

Example 24

Synthesis of α,β,β-trifluorostyrene

Under nitrogen atmosphere, a THF (60 ml) solution of ZnCl$_2$ (5.44 g, 40 mmol) and LiI (10.7 g, 80 mmol) was prepared in a 150-ml pressure glass vessel. Thereafter, a THF solution (2 M, 40 ml, 80 mmol) of PhMgCl was slowly added dropwise while stirring. After the solution was stirred for an hour, a THF solution of Pd$_2$(dba)$_3$(4 mg, 0.01 mol %) was added. After the pressure was slightly reduced, TFE (3 atm) was supplied, and the resulting mixture was stirred for 18 hours in an oil bath at 40° C. After the mixture was cooled to room temperature, the pressure was released, and the reaction vessel was purged with nitrogen. α,α,α-trifluorotoluene (4 mmol) was added dropwise to the reaction solution as an internal standard, and the reaction yield was found by $^{19}$F-NMR (based on the number of moles of the zinc reagent used for the reaction).

Pentane (200 ml) and water (200 ml) was added to the reaction solution, and insoluble matter was removed by Celite filtration. The insoluble matter was washed well with pentane (100 ml). The combined organic layer was washed twice with water (200 ml) and once with saturated saline (30 ml). After the organic layer was dried over anhydrous magnesium sulfate, the anhydrous magnesium sulfate was removed by filtration. The resulting reaction solution was concentrated at normal pressure in a distillation apparatus equipped with a 20-cm Vigreux column, followed by reduced-pressure distillation (boiling point: 58° C./65 mmHg; yield: 2.8 g (44%)).

Product identification was performed by comparing the product with a reference standard using $^{19}$F-NMR and GLC analysis.

GLC Analysis Conditions:
Column: DB-5, Liquid layer=0.25 μm, Diameter=0.2545, Length=30 m
Temperature in vaporizing chamber: 150° C.
Detector temperature: 200° C.
Temperature of constant-temperature bath: 50° C., kept constant for 5 minutes, increased by 10° C./per min to 200° C., kept for 10 minutes.

Example 25

A catalytic reaction was performed while observing the $^{19}$F-NMR spectra using a pressure NMR tube (Wilmad-Lab-Glass, 524-PV-7). A THF-d$_8$/THF solution (0.4 ml; volume ratio=3/1) was added to a solid mixture of ZnCl$_2$ (13.6 mg, 0.100 mmol) and LiI (32.1 mg, 0.240 mmol). A THF solution (1.0 M, 0.200 ml, 0.200 mmol) of C$_6$H$_5$—MgBr, a THF solution (0.5 mM, 20.0 μL, 1.0×10$^{-5}$ mmol) of Pd$_2$(dba)$_3$, and α,α,α-trifluorotoluene (12.3 μL, 0.100 mmol: internal standard for the $^{19}$F-NMR measurement) were added to the resulting solution. The obtained solution was transferred to an NMR tube. After degassing, hexafluoropropene (HFP: 0.313 mmol) was introduced into the NMR tube. The reaction mixture was kept at 40° C. until the reaction was completed (27 hours). The reaction was observed by $^{19}$F-NMR, and it was confirmed that 1-phenyl-1,2,3,3,3-pentafluoro-1-propene (E/Z=2:1) was obtained at a yield of 44% (based on the number of moles of the zinc reagent used for the reaction).

(E)-1-phenyl-1,2,3,3,3-pentafluoro-1-propene $^1$H-NMR (THF-d$_8$): δ 7.26-7.37 (3H), 7.38-7.45 (2H).
$^{19}$F-NMR (THF-d$_8$): δ−174.1 (dq, J$_{FF}$=11, 133 Hz, 1F), −148.0 (dq, J$_{FF}$=22, 133 Hz, 1F), −69.6 (dd, J$_{FF}$=11, 22 Hz, 3F).

(Z)-1-phenyl-1,2,3,3,3-pentafluoro-1-propene $^1$H-NMR (THF-d$_8$): δ 7.26-7.37 (3H), 7.38-7.45 (2H).
$^{19}$F-NMR (THF-d$_8$): δ−159.3 (dq, J$_{FF}$=12, 13 Hz, 1F), −109.9 (dq, J$_{FF}$=12, 8 Hz, 1F), −68.5 (dd, J$_{FF}$=8, 13 Hz, 3F).

Example 26

A catalytic reaction was performed by observing the $^{19}$F-NMR spectra using a pressure NMR tube (Wilmad-LabGlass, 524-PV-7). A THF-d$_8$/THF solution (0.4 ml; volume ratio=3/1) was added to a solid mixture of ZnCl$_2$ (13.6 mg, 0.100 mmol) and LiI (32.1 mg, 0.240 mmol). A THF solution (1.0 M, 0.200 ml, 0.200 mmol) of p-CH$_3$C$_6$H$_4$—MgBr, a THF solution (0.5 mM, 20.0 μL, 1.0×10$^{-5}$ mmol) of Pd$_2$(dba)$_3$, and α,α,α-trifluorotoluene (12.3 μL, 0.100 mmol: internal standard for the $^{19}$F-NMR measurement) were added to the resulting solution. The obtained solution was transferred to an NMR tube. After degassing, HFP (0.313 mmol) was introduced into the NMR tube. The reaction mixture was kept at 40° C. until the reaction was completed (20 hours). The reaction was observed by $^{19}$F-NMR, and it was confirmed that 1-(3-methylphenyl)-1,2,3,3,3-pentafluoro-1-propene (E/Z=3:2) was obtained at a yield of 42% (based on the number of moles of the zinc reagent used for the reaction).

(E)-1-(3-methylphenyl)-1,2,3,3,3-pentafluoro-1-propene $^{19}$F-NMR (THF-d$_8$): δ −69.6 (dd, J=11, 22 Hz, 3F), −148.2 (dq, J=131, 22 Hz, 1F), −174.1 (dq, J=131, 11 Hz, 1F).

(Z)-1-(3-methylphenyl)-1,2,3,3,3-pentafluoro-1-propene $^{19}$F-NMR (THF-d$_8$): δ −68.4 (dd, J=13, 8 Hz, 3F), −109.9 (dq, J=9, 8 Hz, 1F), −159.3 (dq, J=9, 13 Hz, 1F).

The invention claimed is:

1. A method for producing a fluoroolefin substituted with a substituted or unsubstituted aryl or alkyl,
    the method comprising reacting a fluoroolefin selected from the group consisting of tetrafluoroethylene, hexafluoropropylene and trifluoroethylene with an organic magnesium compound in the presence of a fluorophilic compound and a catalyst comprising nickel or palladium,
    to produce the fluoroolefin substituted with the substituted or unsubstituted aryl or alkyl.

2. The method according to claim 1, wherein at least one fluorine atom bonded to a sp$^2$ hybridized carbon atom of the fluoroolefin is substituted with a substituted or unsubstituted aryl or alkyl derived from the organic magnesium compound.

3. The method according to claim 1, further comprising heating.

4. The method according to claim 1, wherein the catalyst comprises palladium.

5. The method according to claim 1, wherein the catalyst comprising palladium is a zerovalent palladium complex, a zerovalent palladium complex produced from a divalent palladium complex during the reaction, or a complex obtained by mixing these complexes with at least one compound selected from the group consisting of a diketone, a phosphine, a diamine and a bipyridyl.

6. The method according to claim 5, wherein:
    the zerovalent palladium complex is at least one member selected from the group consisting of Pd$_2$(DBA)$_3$ (DBA represents dibenzylideneacetone), Pd(COD)$_2$ (COD represents cycloocta-1,5-diene), Pd(DPPE) (DPPE represents 1,2-bisdiphenylphosphinoethane), Pd(PCy$_3$)$_2$ (Cy represents cyclohexyl), Pd(Pt-Bu$_3$)$_2$ and Pd(PPh$_3$)$_4$ (Ph represents phenyl), and
    the phosphine is triarylphosphine or trialkylphosphine.

7. The method according to claim 1, wherein the organic magnesium compound is a compound represented by Formula (7a) and/or Formula (7b):

RMgX (7a)

(R)$_2$Mg (7b)

wherein R is substituted or unsubstituted aryl or alkyl, and X is Cl, Br or I.

8. The method according to claim 7, wherein R is alkyl, or mono-, di- or tri-cyclic aryl,
    wherein the aryl is optionally substituted with at least one member selected from the group consisting of lower alkyl, lower alkenyl, lower alkoxy, and aryl, and
    wherein the alkyl is optionally substituted with at least one member selected from the group consisting of lower alkoxy and aryl.

9. The method according to claim 1, wherein the fluorophilic compound is lithium halide, magnesium halide, or zinc halide.

10. The method according to claim 1, wherein the fluoroolefin substituted with the substituted or unsubstituted aryl or alkyl produced is a compound represented by Formula (4) and/or Formula (5),

wherein R is substituted or unsubstituted aryl or alkyl, and
    the method comprises reacting, in the presence of a fluorophilic compound and a catalyst comprising nickel or palladium, tetrafluoroethylene with an organic magnesium compound represented by Formula (7a) and/or Formula (7b):

RMgX (7a)

(R)$_2$Mg (7b)

wherein X is Cl, Br or I, and R is the same as above.

11. A method for producing a compound represented by Formula (5'),

wherein, R and R' are the same or different, and each represents substituted or unsubstituted aryl or alkyl,
    the method comprising the steps of:
    (i) reacting, in the presence of a fluorophilic compound and a catalyst comprising nickel or palladium, tetrafluoroethylene with an organic magnesium compound represented by Formula (7a) and/or Formula (7b):

RMgX (7a)

(R)$_2$Mg (7b)

wherein X is Cl, Br or I, and R is the same as above,
to produce a compound represented by Formula (4):

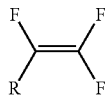 (4)

wherein R is the same as above; and (ii) reacting, in the presence of a fluorophilic compound and a catalyst comprising nickel or palladium, the compound represented by Formula (4) with an organic magnesium compound represented by Formula (7a') and/or Formula (7b'):

R'MgX' (7a')

(R')$_2$Mg (7b')

wherein X is Cl, Br or I, and R' is the same as above,
to produce the compound represented by Formula (5').

12. A method for producing a compound represented by Formula (4a),

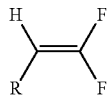 (4a)

wherein R represents substituted or unsubstituted aryl or alkyl, the method comprising reacting, in the presence of a fluorophilic compound and a catalyst comprising nickel or palladium, tetrafluoroethylene with an organic magnesium compound represented by Formula (7a) and/or Formula (7b):

RMgX (7a)

(R)$_2$Mg (7b)

wherein X is Cl, Br or I, and R is the same as above.

* * * * *